Figure 1:
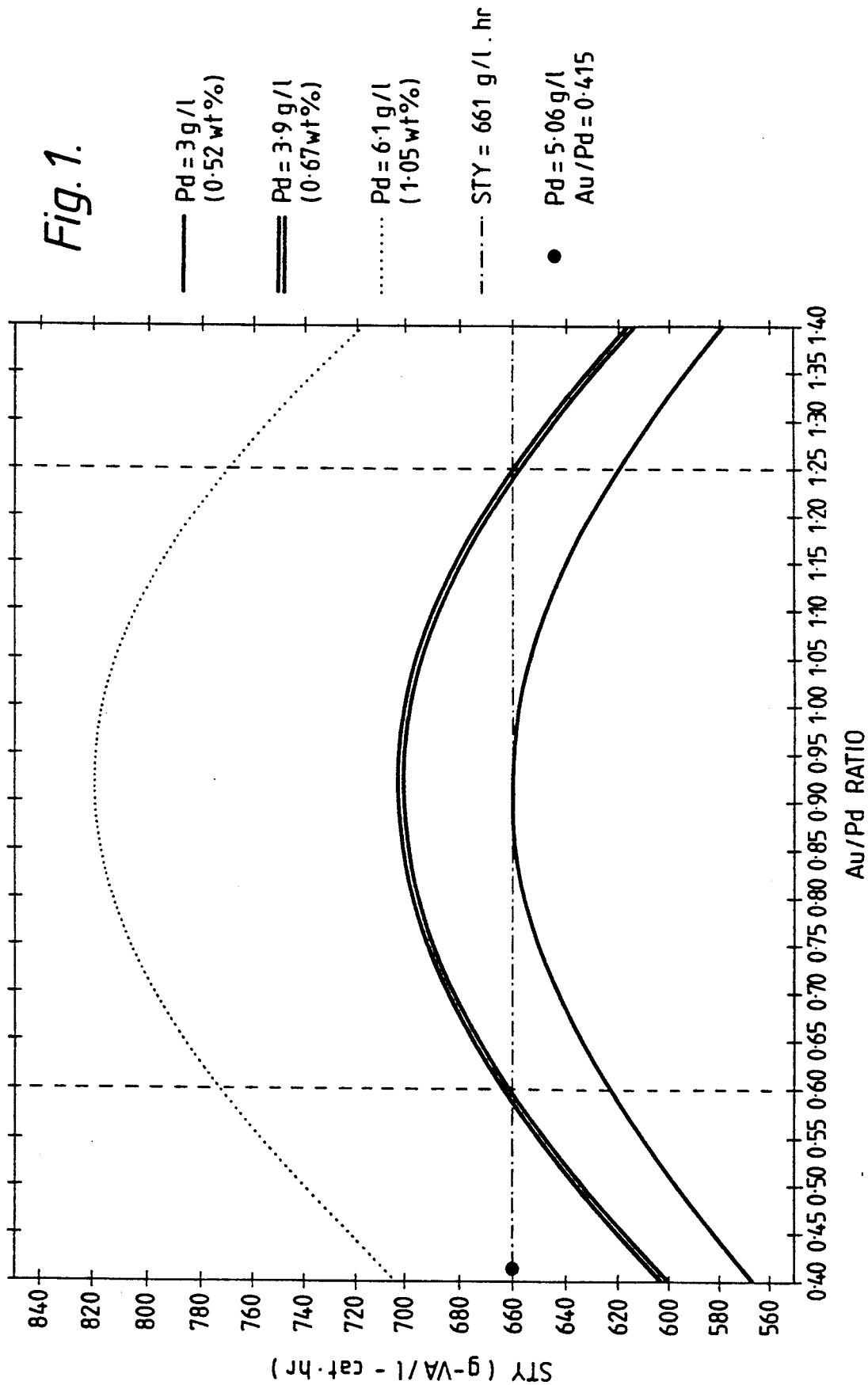

United States Patent [19]

Bartley et al.

[11] Patent Number: 5,274,181
[45] Date of Patent: Dec. 28, 1993

[54] CATALYSTS AND PROCESSES FOR THE MANUFACTURE OF VINYL ACETATE

[75] Inventors: William J. Bartley, Charleston, W. Va.; Simon Jobson, Hull, England; Gordon G. Harkreader, Charleston, W. Va.; Melanie Kitson, Buckinghamshire, England; Mike Lemanski, Cleveland, Ohio

[73] Assignee: BP Chemicals Limited, London, England

[21] Appl. No.: 957,143

[22] Filed: Oct. 7, 1992

Related U.S. Application Data

[62] Division of Ser. No. 696,215, May 6, 1991, Pat. No. 5,185,308.

[51] Int. Cl.$^5$ ............................................. C07C 67/05
[52] U.S. Cl. ..................................................... 560/245
[58] Field of Search .......................................... 560/245

[56] References Cited

U.S. PATENT DOCUMENTS

| | | |
|---|---|---|
| 3,743,607 | 7/1973 | Sennewald et al. |
| 3,761,513 | 9/1973 | Sennewald ............... 560/245 |
| 3,775,342 | 11/1973 | Kronig et al. |
| 3,939,199 | 2/1976 | Fernholz ................... 560/245 |
| 3,969,271 | 7/1976 | Lester . |
| 4,048,096 | 9/1977 | Bissot . |
| 4,087,622 | 5/1978 | Nakamura ................ 560/245 |
| 4,119,567 | 10/1978 | Bartsch ..................... 560/245 |
| 4,133,962 | 1/1979 | Fernholz ................... 560/245 |
| 4,370,492 | 1/1983 | Wunder ..................... 560/245 |
| 4,902,823 | 2/1990 | Wunder ..................... 560/245 |

FOREIGN PATENT DOCUMENTS

| | | |
|---|---|---|
| 1103125 | 2/1968 | United Kingdom . |
| 1283737 | 8/1972 | United Kingdom . |

*Primary Examiner*—Michael L. Shippen
*Attorney, Agent, or Firm*—Brooks, Haidt, Haffner & Delahunty

[57] ABSTRACT

A shell impregnated catalyst for use in the production of vinyl acetate from ethylene, acetic acid and an oxygen containing gas is provided. The catalyst has a productivity of greater than 661 grams of vinyl acetate per hour per liter of catalyst at 150° C. and consists essentially of:

(1) a catalyst support having a particle diameter from about 3 to about 7 mm and a pore volume of 0.2 to 1.5 ml per gram (2) palladium and gold distributed in the outermost 1.0 mm thick layer of the catalyst support particles, and (3) from about 3.5 to 9.5% by weight of potassium acetate.

The catalyst is characterised by having a gold to palladium weight ratio in the range 0.60 to 1.25.

12 Claims, 3 Drawing Sheets

CATALYSTS AND PROCESSES FOR THE MANUFACTURE OF VINYL ACETATE

This application is a division of application Ser. No. 07/696,215, filed May 6, 1991, now U.S. Pat. No. 5,185,308.

The present invention relates to improved palladium/gold catalysts useful in effecting the production of vinyl acetate from ethylene, acetic acid and an oxygen containing gas.

The production of vinyl acetate by reacting ethylene, acetic acid and oxygen together in the gas-phase in the presence of a catalyst containing palladium, gold and an alkali metal acetate promoter is known. The catalyst components are typically supported on a porous carrier material such as silica or alumina.

In early examples of these catalysts, both the palladium and gold were distributed more or less uniformly throughout the carrier (see for example U.S. Pat. Nos. 3,725,680, 3,743,607 and GB 1333449). This was subsequently recognised to be a disadvantage since it was found that the material within the inner part of the carrier did not contribute to the reaction since the reactants did not diffuse significantly into the carrier before reaction occurred. In other words, a significant amount of the palladium and gold never came into contact with the reactants.

In order to overcome this problem, new methods of catalyst manufacture were devised with the aim of producing catalysts in which the active components were concentrated in the outermost shell of the support (shell impregnated catalysts). For example GB 1500167 claims catalysts in which at least 90% of the palladium and gold is distributed in that part of the carrier particle which is not more than 30% of the particle radius from the surface, whist GB 1283737 teaches that the degree of penetration into the porous carrier can be controlled by pretreating the porous carrier with an alkaline solution of for example sodium carbonate or sodium hydroxide.

Another approach which has been found to produce particularly active catalysts is described in U.S. Pat. No. 4,048,096. In this patent shell impregnated catalysts are produced by a process comprising the steps of (1) impregnating a carrier with aqueous solutions of water-soluble palladium and gold compounds, the total volume of the solutions being 95 to 100% of the absorptive capacity of the catalyst support, (2) precipitating water-insoluble palladium and gold compounds on the carrier by soaking the impregnated carrier in a solution of an alkali metal silicate, the amount of alkali metal silicate being such that, after the alkali metal silicate has been in contact with the carrier for 12 to 24 hours, the pH of the solution is from 6.5 to 9.5; (3) converting the water soluble palladium and gold compounds into palladium and gold metal by treatment with a reducing agent; (4) washing with water; (5) contacting the catalyst with alkali metal acetate and (6) drying the catalyst. Using this method, catalysts having a specific activity of at least 83 grams of vinyl acetate per gram of precious metal per hour measured at 150° C. can, if it is alleged, be obtained.

At column 5 of U.S. Pat. No. 4,048,096 it is taught that the process described above is preferably used to prepare catalysts containing 1.65 to 3.3 grams of palladium and 0.75 to 1.5 grams of gold per liter of finished catalyst. For a typical silica support having a density of say 600 grams per liter, these ranges correspond, in % wt. terms, to 0.25 to 0.5% and 0.12 to 0.22% and hence to a Au:Pd % wt. ratio of from 0.16 to 0.75. The amounts of alkali metal acetate taught as being effective are 5 to 60 grams per liter preferably 25 to 35 grams per liter corresponding, in the case of potassium acetate, to 0.75 to 9.2% by weight preferably 3.8 to 5.4%.

Six examples according to the invention are disclosed in U.S. Pat. No. 4,048,096. All of these teach the use of catalysts having a gold to palladium weight ratio in the range 0.42 to 0.45 and a gold content of 2.1 grams per liter or less. The most active catalyst described is that shown in Example 3 which has a gold content of 2.1 grams per liter, a gold to palladium weight ratio of 0.42 and a productivity of 610 grams of vinyl acetate per hour per liter of catalyst at 150° C. Computer predictions of the activity of this catalyst on the basis of data we have obtained during our studies indicates a higher activity at 661.

It has now been found that shell impregnated catalysts having a productivity in excess of 661 grams of vinyl acetate per hour per liter of catalyst at 150° C. can be obtained by ensuring that the weight ratio of gold to palladium is in the range 0.60 to 1.25. Furthermore it has been found that for a given metals loading the productivity can be further improved by ensuring that the potassium acetate content of the catalyst is in the range 3.5 to 9.5% by weight.

This finding is quite unexpected and contrary to the teaching of U.S. Pat. No. 4,048,096 which suggests that a gold to palladium weight ratio of less than 0.5 should be used.

Shell impregnated catalysts are also disclosed in U.S. Pat. No. 4,087,622. At column 2, lines 47 to 50 it is taught that the percentage of gold metal relative to the combined weight of palladium and gold metals in preferably from about 5 to 60 percent by weight. Such figures correspond to a broad range of gold to palladium weight ratios of 0.05 to 1.5 indicating that no significance was attached to the criticality of this variable. Furthermore a broad range of alkali metal acetate contents (1 to 30 weight %) is taught and only catalysts having potassium acetate contents of 3% are exemplified. Examples 4-1 to 4-7 show the effect of varying the gold content of the catalyst relative to a fixed palladium loading but there is nothing to suggest the criticality of the gold to palladium ratio over a wide range of palladium loadings.

According to the present invention there is provided a shell impregnated catalyst for use in the production of vinyl acetate from ethylene, acetic acid and an oxygen containing gas, said catalyst having a productivity of greater than 661 grams of vinyl acetate per hour per liter of catalyst at 150° C. and consisting essentially of:
(1) a catalyst support having a particle diameter from about 3 to about 7 mm and a pore volume of 0.2 to 1.5 ml per gram
(2) palladium and gold distributed in the outermost 1.0 mm thick layer of the catalyst support particles, and
(3) from about 3.5 to about 9.5% by weight of potassium acetate wherein the gold to palladium weight ratio in said catalyst is in the range 0.60 to 1.25.

The catalysts of the present invention have the additional advantage that there are highly selective towards the production of vinyl acetate at the expense of by-products such as carbon dioxide.

Turning to the components of the catalyst it is preferred that the catalyst support is either a porous silica, alumina silica/alumina or titania with the former being most preferred. The support should have a surface area in the range 100–800 $m^2$ per g. As regards the palladium content of the catalyst this is suitably in excess of 2.5 grams per liter of catalyst in order to obtain the high productivities referred to above. For typical catalysts having a sodium content of about 0.5% by weight the palladium content should preferably be greater than 3.0 grams per liter of catalyst, more preferably greater than 3.9 grams per liter of catalyst and most preferably in the range 3.9 to 6.1 grams per liter of catalyst. The gold content on the other hand should suitably be greater than 1.5 grams per liter of catalyst and for catalysts having the above-mentioned sodium content preferably greater than 1.8 grams per liter of catalyst, more preferably greater than 2.3 grams per liter of catalyst and most preferably in the range 2.3 to 7.6 grams per liter of catalyst. Finally it is preferred that the gold to palladium weight ratio is in the range 0.7 to 1.05 most preferably 0.85 to 1.05.

Turning to the potassium acetate content of the catalyst it is preferred that this is in the range 5 to 9% by weight to obtain optimum activity.

In an embodiment of the present invention, it has been found that the level of undesirable ethyl acetate byproduct can be substantially reduced by employing catalysts in which the gold to palladium weight ratio is greater than or equal to about 0.9.

The catalysts of the present invention may conveniently be prepared by the method described in detail in GB 1559540. In the first stage of this process, the support is impregnated with a solution containing the required amounts of palladium and gold in the form of soluble salts. Examples of salts include the soluble halide derivatives. The impregnating solution is preferably an aqueous solution and the volume of solution used is such that is corresponds to between 95 and 100% of the pore volume of the support preferably 98–99%.

After impregnation the wet support is treated with an aqueous solution of an alkali metal salt selected from alkali metal silicates, carbonates or hydroxides. The amount of alkali metal salt used is such that after the solution has been in contact with the impregnated support for between 12 and 24 hours, the pH of the solution is suitably in the range 6.5 to 9.5 preferably 7.5 to 8 when measured at 25° C. Preferred alkali metal salts are sodium metal silicate, sodium carbonate and sodium hydroxide.

During the treatment described above palladium and gold hydroxides are believed to be precipitated or incorporated onto the support. To convert such materials into the metallic state the impregnated support is treated with a reducing agent such as ethylene, hydrazine, formaldehyde or hydrogen. If hydrogen is used it will usually be necessary to heat the catalyst to 100°–300° C. in order to effect complete reduction.

After the steps described above have been carried out, the reduced catalyst is washed with water, impregnated with the required amount of alkali metal acetate and thereafter dried.

The catalysts of the present invention when prepared by the above-mentioned process typically contain 0.5% by weight sodium derived largely from the precipitating agent. As will be described in detail in a further separate patent application it is desirable that the sodium content of such catalysts is less than this figure in order to obtain optimum catalyst productivity. The sodium content of the catalyst can be reduced for example by washing with potassium acetate solution or by the use of non-sodium containing reagents.

Preparation of vinyl acetate using the catalysts of the present invention is typically effected by contacting ethylene, acetic acid and oxygen or air with a sample of the catalyst at a temperature in the range 100° to 200° C., preferably in the range 140° to 180° C., and at pressure in the range atmospheric to 20 bars. Typically the process is carried out heterogeneously with the reactants being present in the gas phase and with levels of oxygen below the limits of flammability. The reaction is usually carried out with an excess of ethylene whilst the amount of acetic acid is determined by dew point considerations. After reaction, the vinyl acetate is separated and purified using conventional methods.

The present invention will now be illustrated with reference to the following Examples.

General Method for Preparing the Catalyst Samples

During this method only de-ionised water was used.

Step (1) Impregnation of the Support 15 grams of a high surface area spherical silica support (KA160-ex Sud Chemie) was added to 8.7 ml of an aqueous solution of $Na_2PdCl_4$ and $HAuCl_4$. The amounts of the palladium and gold complexes used were such as to achieve the desired palladium and gold loadings on the support. The addition was done in a single portion and the mixture was gently swirled until the solution was fully absorbed. After impregnation the impregnated support was allowed to stand for two hours at room temperature.

Step (2) Precipitation

A solution of 18 ml sodium metasilicate in water was quickly added to the wet impregnated support. The concentration of the 18 ml sodium metasilicate solution (SMS) was determined using the following formula:

$$1.8 \times [(1 \text{ mole of SMS/mole } Na_2PdCl_4) + (2 \text{ moles of SMS/mole } HAuCl_4 + (0.02 \text{ millimoles SMS/gram of support}]].$$

The mixture was swirled intermittently over a period of 15 minutes then permitted to stand undisturbed overnight.

Step (3) Reduction

The aqueous phase above the black pellets was treated with an 85% hydrazine hydrate solution. The quantity of hydrazine hydrate used was determined using the formula:

$$22.5 \times [(1 \text{ mole } N_2H_4/\text{mole } Na_2PdCl_4) + (1.5 \text{ mole } N_2H_4/\text{mole } HAuCl_4)].$$

The mixture was gently swirled then allowed to stand undisturbed overnight.

Step (4) Washing

The aqueous phase, which contained a small amount of suspended black solids, was decanted and the spheres were washed four times with about 50 ml water, decanting after each wash. The catalyst was transferred to a glass column fitted with a stopcock and then washed with further water at an approximate rate of one liter per 12 hours until the washings yielded a negative chloride test with silver nitrate solution.

Steps (5)-(7) Drying, Potassium Acetate Loading and Final Drying

The catalyst was dried overnight at 60° C. in a forced air oven, cooled, then impregnated with a solution of the required amount of potassium acetate in 8.7 ml of water. The mixture was swirled until all the liquid was absorbed, then the catalyst was again dried at 60° C. on a stainless steel screen in a forced-air oven.

Catalyst Test Method and Results

Tests were performed at 7.8 barg and 150° C. on 2.5 g samples of the 5-6 mm catalyst pellets, diluted with 30 ml of 1 mm glass beads and loaded into a stainless steel tube of internal diameter 10-11 mm. The catalyst was activated at 7.8 barg by heating at 160° C. for 3 hours in a stream of nitrogen or helium and then at 150° C. for 10 minutes in stream of ethylene. Acetic acid vapour was then mixed with the ethylene and passed over the catalyst for a period of at least one hour. A mixture of 21% oxygen in helium was gradually added to the feed gas while maintaining the maximum catalyst bed temperature 150° C. The catalyst hot spot was maintained at 150° C. for 6 hours and thereafter allowed to fall as the catalyst deactivated. The final composition of the reactant mixture was ethylene:acetic acid:oxygen:helium=53.1:10.4:7.7:28.6 and the total gas hourly space velocity was 3850 hr$^{-1}$. The product stream was analysed in the vapour phase at hourly intervals by means of an on-line gas-liquid chromatograph.

Activity was calculated as grams of vinyl acetate produced per liter of catalyst per hour (space time yield, STY) and selectivity was calculated as the percentage of converged ethylene present in the product. All figures quoted are based on the activities and selectivities measured 20 hours after full oxygen content was reached.

Alternative Method for Preparing the Catalyst Samples

The following is an alternative, improved method of making the catalyst.

Step (1) Impregnation of the Support

The same method as set forth above was used.

Step (2) Precipitation

The same method as set forth above was used except that sodium hydroxide was used as the precipitating agent. The amount of sodium hydroxide used was determined using the formula:

1.8 × [(2 moles of NaOH/mole Na$_2$PdCl$_4$) + (4 moles of NaOH/mole HAuCl$_4$) + (0.04 millimoles of NaOH/gram of support)]

Step (3) Reduction

The same method as set forth above was used.

Step (4) Washing

The product of step (3) was washed with water as set forth above. Potassium acetate (5%) however was used instead of water in the column washing.

Step (5) Drying

The product of step (4) was dried overnight at 60° C. on a stainless steel screen in a forced-air oven.

EXAMPLE 1

Catalyst tests to show the effect of noble metal content on catalyst activity and selectivity Catalysts were prepared according to the first general method described above. The nobel metal contents were varied to produce a statistically designed set of experiments. The compositions of the catalysts tested were determined by XRF analysis and are given in Table 1. The targeted potassium acetate content in each case was 7.0 wt. %, corresponding to 2.8 wt. % of potassium. The support as obtained was found to contain 0.4 wt. % of potassium giving a total potassium content of 3.2 wt. %. The weight of catalyst used for each test was varied in the range of 0.5 to 2.5 g, to allow catalyst activities and selectivities to be measured over a range of conversions. The sodium content of the catalysts was approximately 0.5% by weight.

The test conditions used were as described above. The total flow of reactants was such that for a test on 2.5 g of catalyst the GHSV was 3850 hr$^{-1}$. For tests on smaller quantities of catalyst the total flow rate was maintained, giving rise to variations in the GHSV. Activity, selectivity and oxygen conversion measurements were taken after 20 hrs on stream and are also given in Table 2.

The variations in activity, selectivity and conversion with catalyst composition and weight were best fitted to the following expressions:

Equation 1. $STY = e^y$, where:
$y = 6.76 + 0.40(Pd-0.82) + 0.13(Au/Pd-0.81) -$ $$0.57 (Au/Pd00.81)^2 - 0.16(Cat. Wt.-1.5)$$
$$R^2 = 0.95$$

Equation 2. Selectivity $= 100-e^z$, where:
$z = 1.41 - 0.29(Au/Pd-0.81) + 0.49 (Au/Pd-0.81)^2 -$ $$0.39(K-3.25) + 0.10(Cat. Wt.-1.5) - 0.10 (Cat. Wt.-1.5)^2$$
$$R^2 = 0.74$$

Equation 3. Oxygen Conversion:
$= 24.5 + 10.0(Pd-0.82) + 7.74(Pd-0.82)(Cat. Wt.-1.5) +$ $$1.97(Au/Pd-0.81) - 14.1 (Au/Pd-0.81)^2 + 11.6(Cat. Wt.-1.5)$$
$$R^2 = 0.96$$

The abbreviations used in the expressions are Pd=weight percent palladium in catalyst; Au/Pd=weight ratio of gold to palladium; Cat.Wt=catalyst weight in grams. K=weight percent potassium; STY=space time yield in grams of vinyl acetate per liter of catalyst per hour. The correlation coefficients $R^2$ indicate a good fit to the data.

In order to determine the effect of the catalyst composition at constant conversion equation 3 was rearranged to express catalyst weight as a function of palladium content, gold/palladium ratio and conversion. A representative oxygen conversion of 30% was entered into this function. The catalyst weight terms in equations 1 and 2 were then replaced with the weight function obtained on re-arranging equation 3 to give expressions describing the variation in catalyst activity and selectivity with metals content at constant conversion.

Figure 2:
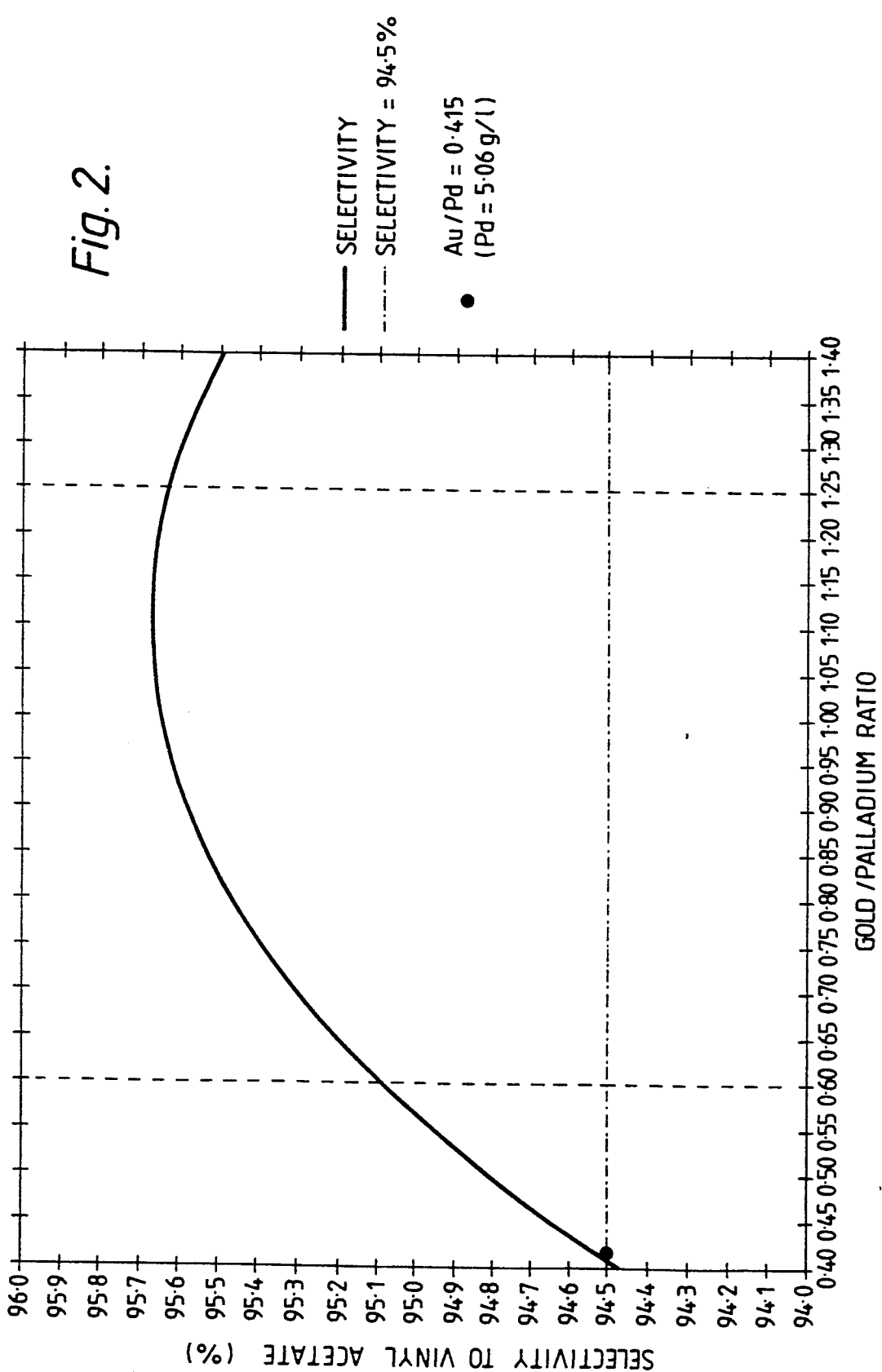

The effect of gold/palladium ratio on activity is shown in FIG. 1, whist the effect on selectivity is shown in FIG. 2. These curves show that improved catalyst activity may be obtained by increasing the palladium loading of the catalyst and by increasing the gold/palladium ratio up to an optimum of 0.9 to 0.95. Further increasing the gold/palladium ratio above this reduces the activity of the catalyst.

Figure 3:
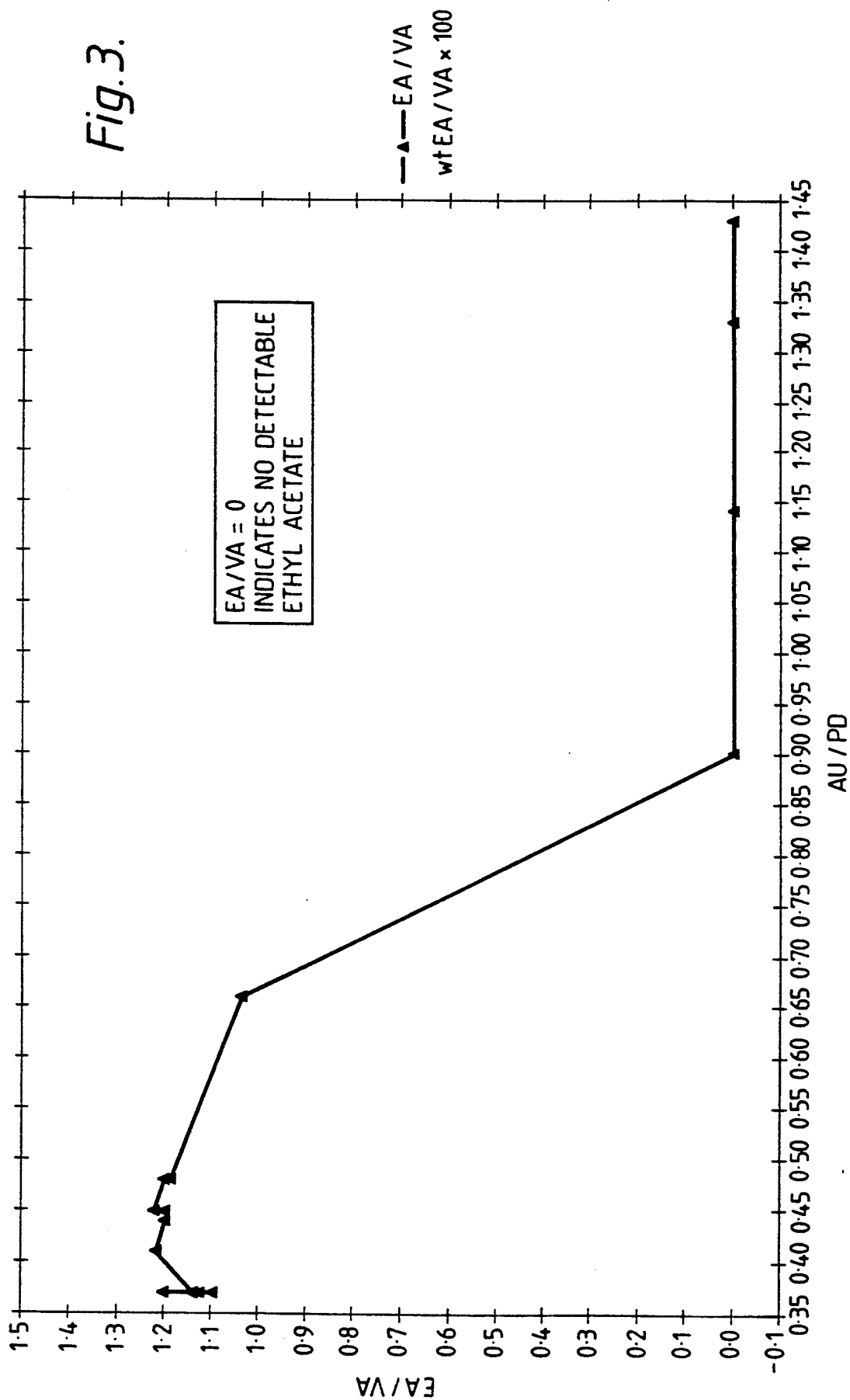

Selectivity increases are also obtained by increasing the gold/palladium ratio. Finally, as can be sen from FIG. 3, catalysts having a gold to palladium ratio of 0.9 or above produce little or no ethyl acetate byproduct.

TABLE 1

Data Used for Modelling STY, Selectivity and Conversion with Palladium Content and Au/Pd Ratio

| Pd wt % | Au wt % | Au/Pd | K wt % | Cat. Wt | STY | Sel. | $O_2$ Conv. |
|---|---|---|---|---|---|---|---|
| | | | | | (measured at 20 hrs) | | |
| 0.58 | 0.26 | 0.45 | 3.3 | 0.77 | 801 | 95.4 | 12.3 |
| 0.58 | 0.26 | 0.45 | 3.3 | 2.49 | 602 | 94.5 | 30.0 |
| 0.88 | 0.42 | 0.48 | 3.3 | 2.50 | 702 | 94.9 | 36.3 |
| 0.91 | 0.34 | 0.37 | 3.2 | 2.50 | 654 | 93.8 | 33.9 |
| 0.91 | 0.34 | 0.37 | 3.2 | 2.50 | 624 | 94.2 | 32.2 |
| 0.91 | 0.34 | 0.37 | 3.2 | 0.76 | 835 | 95.2 | 12.7 |
| 1.01 | 0.44 | 0.44 | 3.1 | 2.50 | 727 | 94.7 | 35.9 |
| 0.91 | 0.34 | 0.37 | 3.2 | 1.25 | 747 | 94.7 | 19.0 |
| 1.06 | 1.21 | 1.14 | 3.1 | 0.85 | 993 | 96.2 | 16.0 |
| 0.58 | 0.83 | 1.43 | 3.2 | 2.50 | 592 | 95.4 | 28.6 |
| 0.58 | 0.83 | 1.43 | 3.2 | 0.80 | 771 | 96.0 | 11.4 |
| 0.92 | 0.83 | 0.90 | 3.1 | 2.46 | 760 | 95.4 | 35.1 |
| 1.00 | 0.87 | 0.87 | 3.1 | 1.55 | 939 | 95.3 | 28.0 |
| 1.01 | 0.44 | 0.44 | 3.1 | 0.80 | 991 | 95.1 | 15.7 |
| 0.91 | 0.34 | 0.37 | 3.2 | 0.50 | 879 | 95.8 | 9.2 |
| 0.91 | 0.34 | 0.37 | 3.2 | 2.09 | 709 | 94.0 | 30.7 |
| 0.74 | 0.49 | 0.66 | 3.3 | 2.50 | 693 | 94.8 | 35.7 |
| 0.70 | 0.29 | 0.41 | 3.4 | 2.50 | 644 | 95.2 | 32.2 |
| 0.88 | 0.42 | 0.48 | 3.3 | 2.50 | 691 | 94.9 | 36.3 |
| 0.87 | 1.16 | 1.33 | 3.2 | 0.85 | 916 | 96.0 | 14.5 |
| 0.58 | 0.26 | 0.45 | 3.3 | 2.48 | 555 | 95.5 | 25.3 |
| 0.92 | 0.83 | 0.90 | 3.1 | 1.48 | 937 | 96.2 | 26.6 |
| 0.87 | 1.16 | 1.33 | 3.2 | 0.89 | 857 | 96.4 | 14.0 |

3.2 wt % K is approximately equal to 7.0 wt % KOAc

We claim:

1. A process for preparing vinyl acetate which comprises reacting ethylene with acetic acid in the presence of an oxygen containing gas at a temperature in the range 100° to 200° C. in the presence of a shell impregnated catalyst having a productivity at greater than 661 grams of vinyl acetate per hour per liter of catalyst at 150° C. and consisting essentially of:
   (1) a catalyst support having a particle diameter from about 3 to about 7 mm and a pore volume of 0.2 to 1.5 ml per gram,
   (2) palladium and gold distributed in the outermost 1.0 mm thick layer of the catalyst support particles, and
   (3) from about 3.5 to about 9.5% by weight of potassium acetate wherein the gold to palladium weight ratio in said catalyst is in the range 0.60 to 1.25.

2. A process as claimed in claim 1 wherein the gold to palladium weight ratio in the catalyst is in the range 0.7 to 1.05.

3. A process as claimed in claim 2 wherein the gold to palladium weight ratio is in the range 0.85 to 1.05.

4. A process as claimed in claim 1 wherein the potassium acetate content of the catalyst is 5 to 9% by weight.

5. A process as claimed in claim 1 wherein the palladium content of the catalyst is greater than 3.0 grams per liter of catalyst.

6. A process as claimed in claim 5 wherein the palladium content is greater than 3.9 grams per liter of catalyst.

7. A process as claimed in claim 6 wherein the palladium content is in the range 3.9 to 6.1 grams per liter of catalyst.

8. A process for preparing vinyl acetate which comprises reacting ethylene with acetic acid in the presence of an oxygen containing gas at a temperature in the range 100° to 200° C. in the presence of a shell impregnated catalyst consisting essentially of:
   (1) a catalyst support having a particle diameter from about 3 to about 7 mm and a pore volume of 0.2 to 1.5 ml per gram,
   (2) palladium and gold distributed in the outermost 1.0 mm thick layer of the catalyst support particles, and
   (3) from about 3.5 to about 9.5% by weight of potassium acetate wherein the gold to palladium weight ratio is greater than or equal to about 0.9.

9. A process as claimed in claim 8 wherein the potassium acetate content of the catalyst is 5 to 9% by weight.

10. A process as claimed in claim 8 wherein the palladium content of the catalyst is greater than 3.0 grams per liter of catalyst.

11. A process as claimed in claim 10 wherein the palladium content is greater than 3.9 grams per liter of catalyst.

12. A process as claimed in claim 11 wherein the palladium content is in the range 3.9 to 6.1 grams per liter catalyst.

* * * * *

UNITED STATES PATENT AND TRADEMARK OFFICE
CERTIFICATE OF CORRECTION

PATENT NO. : 5,274,181
DATED : December 28, 1993
INVENTOR(S) : WILLIAM J. BARTLEY, SIMON JOBSON, GORDON G. HARDRADEER, MELANIE KITSON and MIKE LEMANSKI It is certified that error appears in the above-indentified patent and that said Letters Patent is hereby corrected as shown below:

Col. 1, l. 37, correct the spelling of the word "whilst"

Col. 6, l. 30, in the formula there should be a dash (-) between "Pd" and "0.081"

Col. 7, l. 10, correct the spelling of the word "seen"

Signed and Sealed this

Twenty-fourth Day of May, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,274,181
DATED     : December 28, 1993
INVENTOR(S): WILLIAM J. BARTLEY, SIMON JOBSON, GORDON G. HARDRADEER, MELANIE KITSON and MIKE LEMANSKI It is certified that error appears in the above-indentified patent and that said Letters Patent is hereby corrected as shown below:

Col. 2, line 2, change "0.25 to 0.5%" to --0.25 to 0.54%--

Col. 2, line 2, change "0.12 to 0.22%" to --0.11 to 0.25%--

Col. 2, line 3, change "0.16 to 0.75" to --0.23 to 0.91--

Signed and Sealed this

Third Day of January, 1995

Attest:

BRUCE LEHMAN

Attesting Officer    Commissioner of Patents and Trademarks